US008623781B2

(12) United States Patent
Ahmed et al.

(10) Patent No.: US 8,623,781 B2
(45) Date of Patent: Jan. 7, 2014

(54) OXIDATIVE DEHYDROGENATION OF PROPANE

(75) Inventors: Shakeel Ahmed, Dhahran (SA); Hassan S. Alasiri, Dhahran (SA); Faizur Rahman, Dhahran (SA); Adnan M. J. Al-Amer, Dhahran (SA)

(73) Assignee: King Fahd University of Pretroleum and Minerals, Dhahran (SA)

( * ) Notice: Subject to any disclaimer, the term of this patent is extended or adjusted under 35 U.S.C. 154(b) by 218 days.

(21) Appl. No.: 13/171,116

(22) Filed: Jun. 28, 2011

(65) Prior Publication Data

US 2013/0006030 A1    Jan. 3, 2013

(51) Int. Cl.
 *B01J 23/00* (2006.01)
 *C01G 31/02* (2006.01)
 *C01G 33/00* (2006.01)

(52) U.S. Cl.
 USPC ......... 502/312; 502/321; 502/353; 423/594.8

(58) Field of Classification Search
 USPC .................. 502/312, 321, 353; 423/594.8
 See application file for complete search history.

(56) References Cited

U.S. PATENT DOCUMENTS

| | | | | |
|---|---|---|---|---|
| 4,141,861 | A * | 2/1979 | Courty et al. | 502/302 |
| 5,334,743 | A | 8/1994 | Blanchard et al. | |
| 5,854,172 | A | 12/1998 | Brazdil, Jr. et al. | |
| 6,756,517 | B2 | 6/2004 | Kishimoto et al. | |
| 7,005,402 | B1 * | 2/2006 | Kato et al. | 502/200 |

FOREIGN PATENT DOCUMENTS

| | | |
|---|---|---|
| EP | 0547981 | 6/1993 |
| WO | WO 02051539 A1 * | 7/2002 |
| WO | WO 2006/040863 | 4/2006 |

OTHER PUBLICATIONS

Vivlovskiy et al., "Improvement of catalytic functions of binary V-Sb oxide catalysts for oxidative conversion of isobutane to isobutene," Chemical Engineering Journal 95 (2003) 37-45.*
Kaidong Chen et al., "Kinetics and Mechanism of Oxidative Dehydrogenation of Propane on Vanadium, Molybdenum, and Tungsten Oxides", J. Phys. Chem. B (2000), vol. 104, pp. 1292-1299.
Jason D. Pless et al., "Catalytic oxidative dehydrogenation of propane over Mg-V/Mo oxides", Journal of Catalysis (2004), vol. 223, pp. 419-431.
Gheorghita Mitran et al., "Oxidative dehydrogenation of isobutane over supported V-Mo mixed oxides", J. Serb. Chem. Soc. (2010), vol. 75(8), pp. 1115-1124.

* cited by examiner

*Primary Examiner* — Anthony J Zimmer
(74) *Attorney, Agent, or Firm* — Richard C. Litman

(57) ABSTRACT

The oxidative dehydrogenation of propane provides a highly selective catalyst for the oxidative dehydrogenation of propane to propylene, and a process for preparing the catalyst. The catalyst is a mixed metal oxides catalyst of the general formula $Mo_aV_bO_x$, where the molar ratio of molybdenum to vanadium is between 1:1 and 9:1 (a:b is between 0.5:0.5 and 0.9:0.1) and x is determined according to the oxidation state of the cations present. The catalyst is prepared by mixing the metals by sol-gel technique, heating the gel to dry the mixed oxides, further heating the dried product to induce auto-combustion, washing the product with isopropyl alcohol, and drying with a supercritical $CO_2$ dryer. Oxidative dehydrogenation is carried out by contacting a stream of propane gas with the bulk mixed metal oxides catalyst at a temperature between 350° C. and 550° C. Propylene selectivity of 100% is reached at conversion rates between 1.9% and 4.8%.

8 Claims, 1 Drawing Sheet

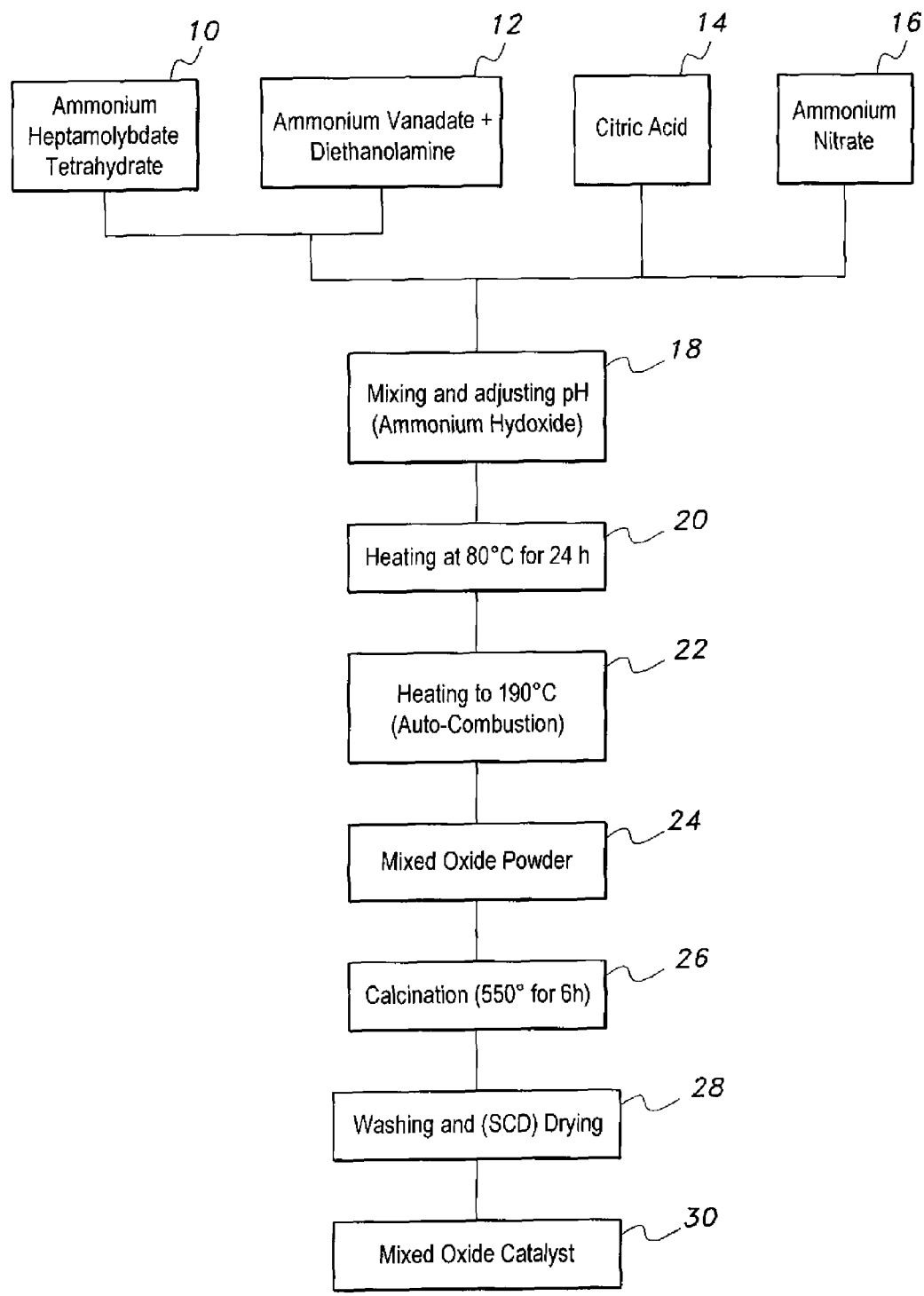

OXIDATIVE DEHYDROGENATION OF PROPANE

BACKGROUND OF THE INVENTION

1. Field of the Invention

The present invention relates to the conversion of alkanes to alkenes, and particularly to the oxidative dehydrogenation of propane to propylene using a mixed metal oxides catalyst that is highly selective for propylene and that permits the reaction to proceed at a milder temperatures than petroleum cracking processes.

2. Description of the Related Art

Propylene is a commercially valuable product. The reactivity of the allylic carbon makes propylene useful for the production of polypropylene, acrylonitrile, propylene oxide, propylene glycol, cumene, and other products, which are useful as final products and as intermediates in the synthesis or production of other commodities.

The majority of propylene is produced by steam hydrocracking of crude petroleum, or by distillation. However, such processes are not highly selective or produce propylene in low yield. Recently, there has been renewed interest in oxidative dehydrogenation of propane for the production of propylene. Oxidative dehydrogenation is attractive because it can be accomplished at lower temperatures than cracking or distillation processes, thereby avoiding complications and expense resulting from coking of the catalyst. Nevertheless, oxidative dehydrogenation is not currently used for the production of propylene, largely due to low yields and lack of selectivity of the currently known catalysts.

Thus, a catalyst for oxidative dehydrogenation of propane solving the aforementioned problems is desired.

SUMMARY OF THE INVENTION

The present invention relates to a highly selective catalyst for the oxidative dehydrogenation of propane to propylene, and a process for preparing the catalyst. The catalyst is a mixed metal oxides catalyst of the general formula $Mo_aV_bO_x$, where the molar ratio of molybdenum to vanadium is between 1:1 and 9:1 (a:b is between 0.5:0.5 and 0.9:0.1) and x is determined according to the oxidation state of the cations present. The catalyst is prepared by mixing the metal precursors by sol-gel technique, heating the gel to dry the mixed oxides, further heating the dried product to induce auto-combustion, washing the product with isopropyl alcohol, and dried with a supercritical $CO_2$ dryer. Oxidative dehydrogenation is carried out by contacting a stream of propane gas with the bulk mixed metal oxides catalyst at a temperature between 350° C. and 550° C. Propylene selectivity of 100% is reached at conversion between 1.9% and 4.8%.

The majority of propylene produced commercially today is by steam cracking and fluid catalytic cracking of petroleum. Because of the harsh conditions of the cracking processes, which require very high temperatures, and depleting reserves of petroleum, oxidative dehydrogenation of propane, which occurs under milder conditions (extending the life of the catalyst by reducing coking) and which may utilize propane derived from alternate sources, e.g., natural gas, has provoked interest. However, propylene is not currently produced on an industrial scale by oxidative dehydrogenation, since currently known catalysts have low selectivity for propylene in combination with low conversion rates. The oxidative dehydrogenation of propane described herein is able to achieve 100% selectivity for propylene.

These and other features of the present invention will become readily apparent upon further review of the following specification and drawings.

BRIEF DESCRIPTION OF THE DRAWINGS

The sole drawing FIGURE is a flowchart showing the steps in a method of preparing a catalyst for the oxidative dehydrogenation of propane.

Similar reference characters denote corresponding features consistently throughout the attached drawings.

DETAILED DESCRIPTION OF THE PREFERRED EMBODIMENTS

The oxidative dehydrogenation of propane provides a highly selective catalyst for the oxidative dehydrogenation of propane to propylene, and a process for preparing the catalyst. The catalyst is a mixed metal oxides catalyst of the general formula $Mo_aV_bO_x$, where the molar ratio of molybdenum to vanadium is between 1:1 and 9:1 (a:b is between 0.5:0.5 and 0.9:0.1) and x is determined according to the oxidation state of the cations present. The catalyst is prepared by mixing the metal precursors by sol-gel technique, heating the gel to dry the mixed oxides, further heating the dried product to induce auto-combustion, washing the product with isopropyl alcohol, and dried with a supercritical $CO_2$ dryer. Oxidative dehydrogenation is carried out by contacting a stream of propane gas with the bulk mixed metal oxides catalyst at a temperature between 350° C. and 550° C. Propylene selectivity of 100% is reached at conversion rates between 1.9% and 4.8%.

The majority of propylene produced commercially today is by steam cracking and fluid catalytic cracking of petroleum. Because of the harsh conditions of the cracking processes, which require very high temperatures, and depleting reserves of petroleum, oxidative dehydrogenation of propane, which occurs under milder conditions (extending the life of the catalyst by reducing coking) and which may utilize propane derived from alternate sources, e.g., natural gas, has provoked interest. However, propylene is not currently produced on an industrial scale by oxidative dehydrogenation, since currently known catalysts have low selectivity for propylene in combination with low conversion rates. The oxidative dehydrogenation of propane described herein is able to achieve 100% selectivity for propylene.

The flowchart in the sole drawing FIGURE illustrates the general steps in the process for preparing the catalyst. The precursors include aqueous solutions of molybdenum and vanadium salts 10, 12, and an aqueous solution of citric acid and ammonium nitrate 14, 16, which are mixed together at step 18, adjusting the pH to obtain a basic gel. The gel is heated at 80° C. for about twenty-four hours to dry the gel, as shown at step 20. The dried product is then heated further until auto-combustion occurs, at about 190° C. (step 22). The combustion product is then ground and crushed to form a powder at step 24, and the powder is calcined at 550° C. for about six hours at step 26. The powder is then washed with isopropyl alcohol, and subjected to supercritical drying with $CO_2$ at step 28. The result is a bulk mixed metal oxide catalyst, obtained at step 30.

The bulk mixed metal oxide catalyst may be used in a fixed bed reactor, a circulating or fluid bed reactor, or a membrane reactor. The process typically involves contacting a stream of propane gas with the bulk metal oxide catalyst by passing the stream over or through a bed of the catalyst, collecting the output, and separating propylene from the output.

EXAMPLES

Crystalline MoVO$_x$ powders were successfully prepared by using an auto-combustion method of nitrate citrate gels. The reagents used for making the catalyst are: ammonium heptamolybdate tetrahydrate (NH$_4$)$_6$Mo$_7$O$_{24}$.4H$_2$O, ammonium vanadate, NH$_4$VO$_3$, ammonium nitrate, citric acid, and diethanolamine as starting materials. Molybdenum solution was prepared by dissolving ammonium heptamolybdate tetrahydrate in distilled water. Vanadium solution was prepared by dissolving ammonium vanadate in distilled water, and diethanolamine was added to the vanadium solution. The molybdenum solution and vanadium solutions were mixed together. A solution of citric acid and ammonium nitrate were mixed with the molybdenum and vanadium solution. To adjust the pH, ammonium hydroxide solution was added drop-wise to achieve a pH of 9.0. This homogeneous solution was heated at 80° C. on an oil bath for twenty-four hours under constant stirring. The solution became dried gel. The temperature of the oil bath was increased to 190° C., and finally the decomposed gel self-ignited. The product was ground and crushed to convert it into powder. The powders were calcined at 550° C. for six hours with a heating rate of 1° C./min. After calcination, catalysts were washed with alcohol and dried by using supercritical CO$_2$ dryer (SCD). All catalysts were prepared under these conditions. The citric acid/metal nitrates ratio (CIM) was 2.0. Ammonium nitrate was added to regulate the fuel/oxidant ratio (F/O), represented by the citric acid/total nitrate ions ratio, which was 0.4. Finally, ammonia solution was slowly added to adjust the pH to 9.

A dramatic improvement in propylene selectivity was achieved by washing the metal oxide catalysts with isopropyl alcohol and drying in a supercritical (CO$_2$) dryer. Catalysts were washed by isopropyl alcohol after calcination and were placed in an ultrasonic bath for thirty minutes to disperse agglomerated solid particles. The solution was filtered by using micro-filter of 0.2 micron, and the filtrate was dried using supercritical CO$_2$ drying (SCD) equipment (Autosam-dri-815B, Series A).

Example 1

Comparative Example

In a comparative example, a MoVO$_{5.5}$ catalyst (referred to as Catalyst A) was prepared with 1:1 molar oxide ratio of Mo:V according to the method described above. The catalyst was tested for oxidative dehydrogenation (OXDH) of propane without washing and drying steps, i.e., without washing with isopropyl alcohol and supercritical CO$_2$ drying. The results are provided in Table 1. At lower temperatures (350-400° C.), no propylene was produced. The main product in the gaseous phase was CO$_2$. Maximum selectivity (11.18%) for propylene was achieved at 550° C. at a propane conversion of 12.74%.

TABLE 1

| OXDH of propane - Catalyst A (Mo$_{0.5}$V$_{0.5}$O$_{5.5}$) | | | | |
|---|---|---|---|---|
| Temperature (° C.) | Propane Conversion (%) | Propylene Selectivity (%) | CO$_2$ Selectivity (%) | CO Selectivity (%) |
| 350 | 4.04 | 0 | 100 | 0 |
| 400 | 4.8 | 0 | 100 | 0 |
| 450 | 6.99 | 3.1 | 96.9 | 0 |
| 500 | 11.15 | 5.96 | 87.82 | 6.22 |
| 550 | 12.74 | 11.18 | 78.31 | 10.51 |

Example 2

Catalyst B was prepared by washing Catalyst A with isopropyl alcohol and placing the mixture in an ultrasonic bath for thirty minutes. After that the mixture was filtered with a 0.20 µM pore size polytetrafluoroethylene (PTFE) filter. The filtrate was dried using supercritical CO$_2$ drying (SCD) equipment. Catalyst B was evaluated for OXDH of propane and the results are provided in Table 2. Propylene with 100% selectivity was obtained in the temperature range of 350-450° C. Above 450° C., the selectivity for propylene was observed to be decreasing, and oxides of carbon (CO$_x$, the more thermodynamically stable oxidation products) were starting to be produced.

TABLE 2

| OXDH of propane - Catalyst B (Mo$_{0.5}$V$_{0.5}$O$_{5.5}$ - SCD) | | | | |
|---|---|---|---|---|
| Temperature (° C.) | Propane Conversion (%) | Propylene Selectivity (%) | CO$_2$ Selectivity (%) | CO Selectivity (%) |
| 350 | 2.74 | 100.00 | 0.00 | 0.00 |
| 400 | 2.94 | 100.00 | 0.00 | 0.00 |
| 450 | 3.43 | 100.00 | 0.00 | 0.00 |
| 500 | 7.66 | 31.62 | 0.00 | 68.38 |
| 550 | 9.84 | 26.61 | 23.08 | 50.31 |

Example 3

Catalyst C was prepared following the same procedure adopted for making Catalyst B, but with a 0.7:0.3 molar oxide ratio of Mo:V. The results of OXDH of propane are presented in Table 3. The catalyst showed no activity up to 400° C. However, at 450° C., 100% selectivity for propylene with 1.9% conversion of propane was achieved. At 500° C. and above, selectivity started decreasing and the major products were oxides of carbon (CO$_x$), indicating the beginning of deep oxidation.

TABLE 3

| OXDH of propane - Catalyst C (Mo$_{0.7}$V$_{0.3}$O$_{2.85}$ - SCD) | | | | |
|---|---|---|---|---|
| Temperature (° C.) | Propane Conversion (%) | Propylene Selectivity (%) | CO$_2$ Selectivity (%) | CO Selectivity (%) |
| 350 | 0.0 | 0.0 | 0.0 | 0.0 |
| 400 | 0.0 | 0.0 | 0.0 | 0.0 |
| 450 | 1.9 | 100.00 | 0.00 | 0.00 |
| 500 | 2.6 | 17.67 | 23.09 | 59.24 |
| 550 | 4.1 | 13.97 | 33.38 | 52.64 |

Example 4

Catalyst D was prepared following the same procedure as adopted for making Catalyst B, but with a 0.8:0.2 molar oxide ratio of Mo:V. The results of OXDH of propane are presented in Table 4. The catalyst showed low activity at 400° C. (only 0.6% conversion). However, at 450° C., 100% selectivity for propylene with 2.1% conversion of propane was achieved. At 500° C. and above, selectivity started decreasing, and the major products were oxides of carbon ($CO_x$), indicating the beginning of deep oxidation.

TABLE 4

OXDH of propane - Catalyst D ($Mo_{0.8}V_{0.2}O_{2.90}$ - SCD)

| Temperature (° C.) | Propane Conversion (%) | Propylene Selectivity (%) | $CO_2$ Selectivity (%) | CO Selectivity (%) |
|---|---|---|---|---|
| 350 | 0.0 | 0.0 | 0.0 | 0.0 |
| 400 | 0.6 | 100.00 | 0.00 | 0.00 |
| 450 | 2.1 | 100.00 | 0.00 | 0.00 |
| 500 | 3.3 | 16.38 | 27.75 | 55.88 |
| 550 | 4.7 | 24.40 | 37.62 | 37.98 |

Example 5

Catalyst E was prepared following the same procedure as adopted for making Catalyst B, but with a 0.9:0.1 molar oxide ratio of Mo:V. The results of OXDH of propane are presented in Table 5. The catalyst showed no activity at 400° C. However, at 450° C., 100% selectivity for propylene with 2.7% conversion of propane was achieved. In this case, even at 500° C., 100% selectivity for propylene with 4.8% conversion of propane was achieved. At 550° C., selectivity decreased substantially, and the major products were oxides of carbon ($CO_x$), indicating the beginning of deep oxidation.

TABLE 5

OXDH of propane - Catalyst E ($Mo_{0.9}V_{0.1}O_{2.95}$ - SCD)

| Temperature (° C.) | Propane Conversion (%) | Propylene Selectivity (%) | $CO_2$ Selectivity (%) | CO Selectivity (%) |
|---|---|---|---|---|
| 350 | 0.0 | 0.0 | 0.0 | 0.0 |
| 400 | 0.0 | 0.0 | 0.0 | 0.0 |
| 450 | 2.7 | 100.00 | 0.00 | 0.00 |
| 500 | 4.8 | 100.00 | 0.00 | 0.00 |
| 550 | 5.8 | 15.07 | 48.68 | 36.25 |

It is to be understood that the present invention is not limited to the embodiments described above, but encompasses any and all embodiments within the scope of the following claims.

We claim:

1. A process of making a bulk mixed metal oxide catalyst for oxidative dehydrogenation of propane to propylene, comprising the steps of:
   forming a gel of mixed molybdenum/vanadium oxides by sol-gel technique;
   heating the gel to dry the gel;
   increasing the heat applied to the dried gel until autocombustion occurs, thereby producing a combustion product;
   grinding and crushing the combustion product to form a mixed metal oxides powder;
   calcining the mixed metal oxides powder;
   washing the calcined mixed metal oxides powder with an organic solvent; and
   drying the washed mixed metal oxides powder in supercritical $CO_2$ to form the mixed metal oxides catalyst.

2. The process of making a bulk mixed metal oxide catalyst according to claim 1, wherein said step of forming a gel comprises the steps of:
   mixing an aqueous solution of a molybdenum salt with an aqueous solution of a vanadium salt;
   mixing an aqueous solution of citric acid with an aqueous solution of ammonium nitrate; and
   mixing the solution of molybdenum and vanadium salts with the citric acid/ammonium nitrate solution to form the gel.

3. The process of making a bulk mixed metal oxide catalyst according to claim 2, wherein the step of forming the gel of mixed molybdenum/vanadium oxides by the sol-gel technique includes the step of adding a base to the gel in order to maintain the pH at about 9.0.

4. The process of making a bulk mixed metal oxide catalyst according to claim 3, wherein the molar ratio of molybdenum to vanadium is between 1:1 and 9:1.

5. The process of making a bulk mixed metal oxide catalyst according to claim 1, wherein said step of heating the gel comprises heating the gel at about 80° C. for about twenty-four hours.

6. The process of making a bulk mixed metal oxide catalyst according to claim 1, wherein said step of increasing the heat comprises heating the dried gel to about 190° C.

7. The process of making a bulk mixed metal oxide catalyst according to claim 1, wherein said organic solvent comprises isopropyl alcohol.

8. The process of making a bulk mixed metal oxide catalyst according to claim 1, wherein the mixed metal oxides catalyst is of the general formula $Mo_aV_bO_x$, wherein the molar ratio of a:b is between 0.5:0.5 and 0.9:0.1, and wherein x is determined according to the oxidation state of the cations present.

* * * * *